(12) United States Patent
Futamura et al.

(10) Patent No.: US 10,687,772 B2
(45) Date of Patent: Jun. 23, 2020

(54) DYNAMIC ANALYSIS APPARATUS

(71) Applicant: Konica Minolta, Inc., Tokyo (JP)

(72) Inventors: Hitoshi Futamura, Hachioji (JP);
Koichi Fujiwara, Osaka (JP); Sho Noji, Kokubunji (JP); Akinori Tsunomori, Kodaira (JP)

(73) Assignee: KONICA MINOLTA, INC., Tokyo (JP)

( * ) Notice: Subject to any disclaimer, the term of this patent is extended or adjusted under 35 U.S.C. 154(b) by 354 days.

(21) Appl. No.: 15/639,084

(22) Filed: Jun. 30, 2017

(65) Prior Publication Data
US 2018/0014802 A1    Jan. 18, 2018

(30) Foreign Application Priority Data

Jul. 15, 2016  (JP) ................. 2016-140439

(51) Int. Cl.
*G06K 9/00* (2006.01)
*A61B 6/00* (2006.01)
(Continued)

(52) U.S. Cl.
CPC ............ *A61B 6/461* (2013.01); *A61B 6/5264* (2013.01); *G06K 9/3233* (2013.01); *G06T 5/002* (2013.01); *G06T 5/50* (2013.01); *G06T 7/246* (2017.01); *G06T 7/254* (2017.01); *G06K 2209/05* (2013.01); *G06T 2207/10016* (2013.01); *G06T 2207/10096* (2013.01); *G06T 2207/10116* (2013.01); *G06T 2207/20021* (2013.01);
(Continued)

(58) Field of Classification Search
CPC ...... A61B 6/461; G06K 9/3233; G06T 5/002; G06T 2207/10096
See application file for complete search history.

(56) References Cited

U.S. PATENT DOCUMENTS

| 7,826,884 B2 * | 11/2010 | Baumgart ............. A61B 6/463 378/62 |
| 8,299,413 B2 * | 10/2012 | Vogt ......................... G06T 5/50 250/208.1 |
| 2015/0313558 A1 * | 11/2015 | Melman .................. G21K 1/04 378/62 |

FOREIGN PATENT DOCUMENTS

| JP | 2012000297 A | 1/2012 |
| JP | 2015043894 A | 3/2015 |
| WO | 2012/026145 A1 | 3/2012 |

OTHER PUBLICATIONS

JPO, Office Action for the corresponding Japanese patent application No. 2016-140439, dated Mar. 17, 2020, with English translation.

* cited by examiner

*Primary Examiner* — Shefali D Goradia
(74) *Attorney, Agent, or Firm* — Lucas & Mercanti, LLP

(57) ABSTRACT

A dynamic analysis apparatus includes: an obtainment unit configured to set a region of interest in dynamic images obtained by photographing a dynamic state by irradiation of a check target part with radial rays, and obtain movement information on movement of the region of interest; a determination unit configured to determine an emphasis level of a pixel signal value of an attentional pixel corresponding to a pixel in the region of interest on the basis of the movement information of the region of interest obtained by the obtainment unit; and a correction unit configured to correct the pixel signal value of the attentional pixel of the dynamic images or analysis result images generated by analyzing the dynamic images, on the basis of the emphasis level determined by the determination unit.

12 Claims, 9 Drawing Sheets

(51) Int. Cl.
*G06K 9/32* (2006.01)
*G06T 5/00* (2006.01)
*G06T 7/246* (2017.01)
*G06T 7/254* (2017.01)
*G06T 5/50* (2006.01)
(52) U.S. Cl.
CPC ............... *G06T 2207/20104* (2013.01); *G06T 2207/30008* (2013.01); *G06T 2207/30061* (2013.01)

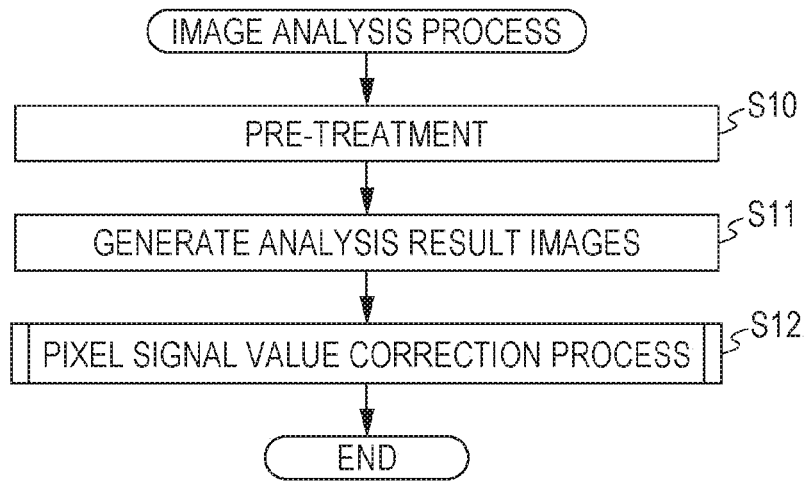
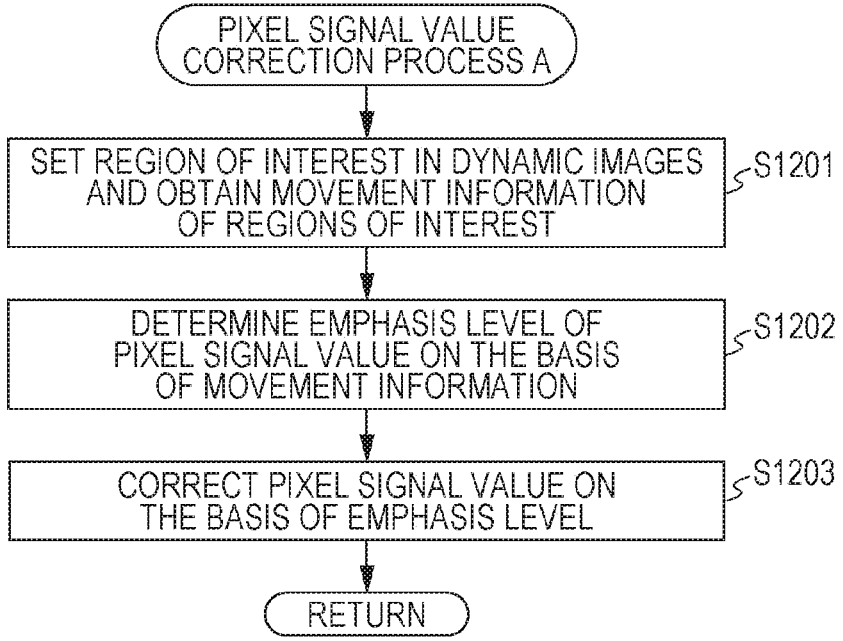

DYNAMIC ANALYSIS APPARATUS

The entire disclosure of Japanese Patent Application No. 2016-140439 filed on Jul. 15, 2016 including description, claims, drawings, and abstract are incorporated herein by reference in its entirety.

BACKGROUND OF THE INVENTION

Field of the Invention

The present invention relates to a dynamic analysis apparatus.

Description of the Related Art

A technique of photographing the dynamic state of a chest part, analyzing the obtained dynamic images, and using the images in the diagnosis has been known. The dynamic images of the chest part include, for example, the movements of the skeleton and the like along with the respiration and the pulsation of a heart. An artifact by these movements is emphasized in the general dynamic analysis process based on the difference process for the interframe difference or the like, and the emphasized artifact interrupts the observation of the signals which should be focused. As a result, the accuracy of analysis and diagnosis has deteriorated.

One of the solutions is described in, for example, "Development of low-cost and low-dose portable functional X-ray imaging (Visual stethoscope)" in Japanese journal of imaging and information sciences in medicine, Vol 31, No. 2, 2014 written by Rie TANAKA and Shigeru SANADA. In this journal, the soft-tissue motion image is generated by performing the bone suppression process on the chest dynamic images (original image), and from the generated soft-tissue motion image, the pulmonary ventilation mapping image (interframe difference image) is generated; thus, the rib artifact is suppressed as compared to that on the pulmonary ventilation mapping image generated from the original image. Moreover, JP 2015-43894 A has described that the X-ray motion image related to the soft tissue is generated by eliminating the bone shadow from the X-ray motion image and based on the generated X-ray motion image, the soft tissue can be analyzed with high accuracy.

However, the bone suppression process does not suppress the bone shadow for sure and may leave some ribs visible in a certain region, in which case the artifact cannot be entirely eliminated. As a result, the artifact appears differently depending on the places and the user cannot easily know the behavior of the process. Especially a doctor who needs to interpret a large amount of radiography in the limited time finds it complicated to do it while considering the level of every artifact, and this deteriorates the diagnosis efficiency.

According to "Development of low-cost and low-dose portable functional X-ray imaging (Visual stethoscope)" in Japanese journal of imaging and information sciences in medicine, Vol 31, No. 2, 2014 written by Rie TANAKA and Shigeru SANADA, the bone suppression process takes 15 seconds per image, and if this process applies to all the frame images of the dynamic images, it is impossible to execute the diagnosis while referring to the analysis result immediately after the photographing.

SUMMARY OF THE INVENTION

An object of the present invention to suppress in a short time and with high accuracy, an artifact in dynamic images or analysis result images thereof caused by the movement of a structure or the like along with the respiration or the pulsation of a heart.

To achieve the abovementioned object, according to an aspect, a dynamic analysis apparatus reflecting one aspect of the present invention comprises:

an obtainment unit configured to set a region of interest in dynamic images obtained by photographing a dynamic state by irradiation of a check target part with radial rays, and obtain movement information on movement of the region of interest;

a determination unit configured to determine an emphasis level of a pixel signal value of an attentional pixel corresponding to a pixel in the region of interest on the basis of the movement information of the region of interest obtained by the obtainment unit; and a correction unit configured to correct the pixel signal value of the attentional pixel of the dynamic images or analysis result images generated by analyzing the dynamic images, on the basis of the emphasis level determined by the determination unit.

According to an invention of Item. 2, in the dynamic analysis apparatus of Item. 1, the movement information preferably includes a movement amount, and the determination unit preferably determines the emphasis level to be a lower emphasis level as the movement amount of the region of interest is larger.

According to an invention of Item. 3, in the dynamic analysis apparatus of Item. 1 or 2, the dynamic analysis apparatus preferably further comprises a second obtainment unit configured to set a reference region in the dynamic images, and obtain movement information on movement of a structure included in the reference region, and the determination unit preferably determines the emphasis level on the basis of the movement information of the region of interest and the movement information of the structure included in the reference region.

According to an invention of Item. 4, in the dynamic analysis apparatus of Item. 3, the movement information of the region of interest and the movement information of the structure included in the reference region preferably include a movement direction, and the determination unit preferably determines the emphasis level on the basis of an angle difference between the movement direction of the region of interest and the movement direction of the structure included in the reference region.

According to an invention of Item. 5, in the dynamic analysis apparatus of Item. 4, the dynamic images are preferably dynamic images of a chest part, the second obtainment unit preferably sets a reference region in a region including a diaphragm of the dynamic images and obtains a movement direction of the diaphragm, and the determination unit preferably determines the emphasis level to be a lower emphasis level as the angle difference between the movement direction of the region of interest and the movement direction of the diaphragm is larger.

According to an invention of Item. 6, in the dynamic analysis apparatus of Item. 4, the dynamic images are preferably dynamic images of a chest part, the second obtainment unit preferably sets a reference region in a region including a shoulder of the dynamic images and obtains a movement direction of the shoulder, and the determination unit preferably determines the emphasis level to be a lower emphasis level as the angle difference between the movement direction of the region of interest and the movement direction of the shoulder is smaller.

According to an invention of Item. 7, in the dynamic analysis apparatus of Item. 1 or 2, the movement information preferably includes a movement direction, and a specification unit configured to set a reference region in the dynamic images and specify a movement direction of a predetermined structure on the basis of a change of a pixel signal value in the reference region is preferably provided, and the determination unit preferably determines the emphasis level on the basis of an angle difference between the movement direction of the region of interest and the movement direction of the predetermined structure.

According to an invention of Item. 8, in the dynamic analysis apparatus of Item. 7, the dynamic images are preferably dynamic images of a chest part, the specification unit preferably sets the reference region in a region between ribs of the dynamic images and specifies a movement direction of the ribs on the basis of the change of the pixel signal value in the reference region, and the determination unit preferably determines the emphasis level to be a lower emphasis level as the angle difference between the movement direction of the region of interest and the movement direction of the ribs is smaller.

According to an invention of Item. 9, in the dynamic analysis apparatus of Item. 1 or 2, the determination unit preferably determines the emphasis level in accordance with a relation table or graph expressing the emphasis level relative to the movement information of the region of interest.

According to an invention of Item. 10, in the dynamic analysis apparatus of any one of Items. 4 to 8, the determination unit preferably determines the emphasis level in accordance with a relation table or graph expressing the emphasis level relative to the movement information of the region of interest and the angle difference.

According to an invention of Item. 11, in the dynamic analysis apparatus of any one of Items. 4 to 8, the determination unit preferably determines the emphasis level in accordance with a relation table or graph expressing the emphasis level relative to the movement information of the region of interest and an angle obtained by subtracting the angle difference from $\pi$.

According to an invention of Item. 12, in the dynamic analysis apparatus of any one of Items. 1 to 11, the analysis result image is preferably an interframe difference image generated by calculating a difference value of corresponding pixels between frame images in the dynamic images.

BRIEF DESCRIPTION OF THE DRAWINGS

The above and other objects, advantages and features of the present invention will become more fully understood from the detailed description given hereinbelow and the appended drawings which are given by way of illustration only, and thus are not intended as a definition of the limits of the present invention, and wherein:

FIG. 3 is a flowchart showing an image analysis process to be executed by a control unit of a diagnosis console of FIG. 1;

FIG. 4 is a flowchart showing a pixel signal value correction process A to be executed in step S12 in FIG. 3 according to a first embodiment;

DESCRIPTION OF THE PREFERRED EMBODIMENTS

Hereinafter, an embodiment of the present invention will be described in detail with reference to the drawings. However, the scope of the invention is not limited to the illustrated examples.

First Embodiment

[Structure of Dynamic Analysis System 100]

First, a structure is described.

Figure 1:
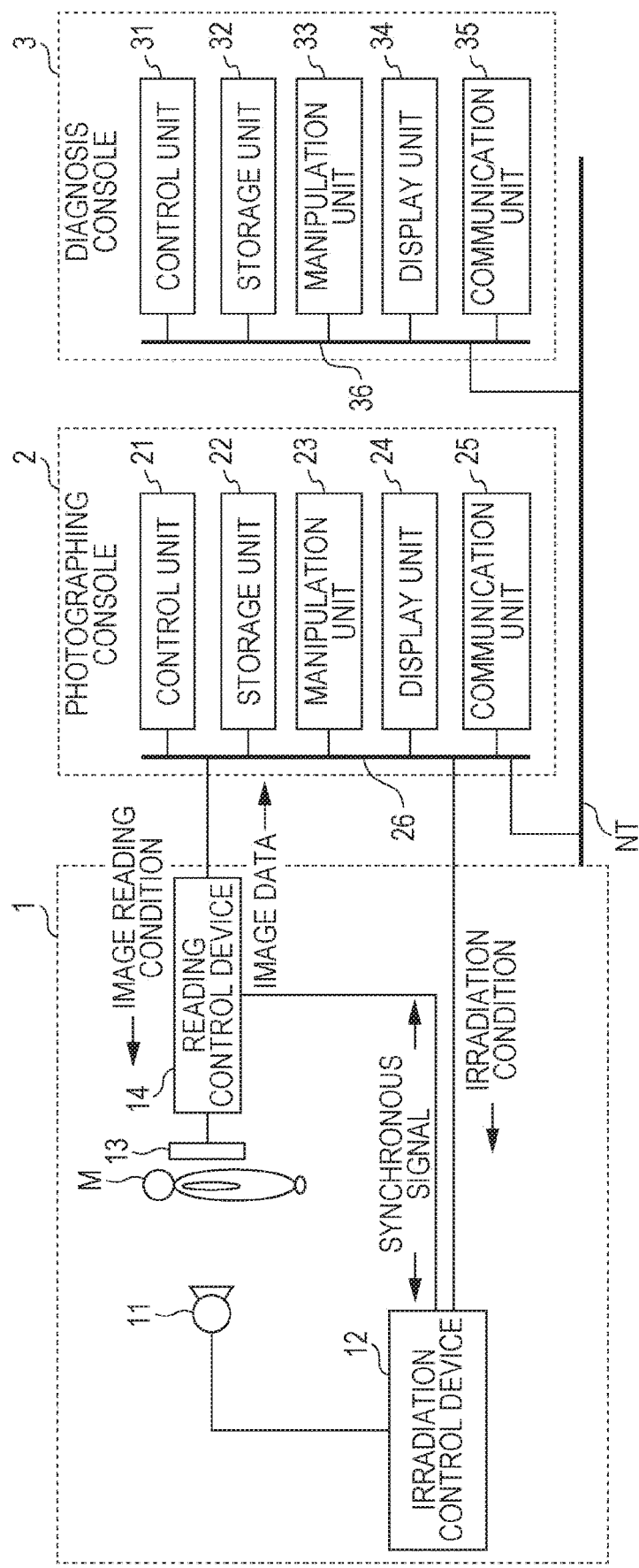
FIG. 1 is a diagram illustrating an entire structure of a dynamic analysis system according to an embodiment of the present invention.

FIG. 1 illustrates the entire structure of a dynamic analysis system 100 in the present embodiment.

As illustrated in FIG. 1, in the dynamic analysis system 100, a photographing device 1 and a photographing console 2 are connected to each other through a communication cable or the like, and the photographing console 2 and a diagnosis console 3 are connected to each other through a communication network NT such as a LAN (Local Area Network). Although the photographing console 2 and the diagnosis console 3 are connected with a wire to a communication network NT in the present embodiment, the photographing console 2 and the diagnosis console 3 may alternatively be connected without a wire.

[Structure of Photographing Device 1]

The photographing device 1 is a photographing unit configured to photograph the dynamic state of a human body with a periodicity (cycle) such as the form change of a lung in expansion and contraction along with the respiratory movement, the pulsation of a heart, and the like. Photographing the dynamic state refers to obtaining a plurality of images by repeatedly irradiating a subject M with the radial rays such as X-rays in a pulsed manner at predetermined time intervals (pulsed irradiation) or continuously irradiating the subject M with the radial rays such as X-rays at low dose rate (continuous irradiation). A series of images obtained by the photographing of the dynamic state is called the dynamic images. Each of the plurality of images constituting the dynamic images is called a frame image. In the embodiment below, description is made of an example in which the photographing of the dynamic state is performed by the pulsed irradiation.

A radiation source 11 is disposed to face a radiation detector 13 with a subject M interposed therebetween, and emits radiation rays (X-rays) to the subject M in accordance with the control of an irradiation control device 12.

The irradiation control device 12 is connected to the photographing console 2, and controls the radiation source 11 on the basis of an irradiation condition input from the photographing console 2 to perform the radiographing. The irradiation condition input from the photographing console 2 includes, for example, the pulse rate, the pulse width, the pulse interval, the number of photographing frames in one photographing time, the value of X-ray tube current, the value of X-ray tube voltage, the type of grid, the additional filter type, or the like. The pulse rate is the number of irradiation shots per second, and coincides with the frame rate to be described below. The pulse width is the irradiation length of time per shot. The pulse interval is the time after the start of one irradiation and before the start of the next irradiation, and coincides with the frame interval to be described below.

The radiation detector 13 includes a semiconductor image sensor such as an FPD. The FPD includes, for example, a glass substrate or the like and has a plurality of detection elements (pixels) arranged in matrix at predetermined positions on the substrate. The detection element detects the radiation rays, which are emitted from the radiation source 11 and transmit through at least the subject M, in accordance with the intensity thereof, converts the detected radiation rays into electric signals, and then accumulates the signals. Each pixel includes a switching unit such as a TFT (Thin Film Transistor). In regard to FPDs, there are the indirect conversion type that converts the X-rays into electric signals through a scintillator by a photoelectric conversion element, and the direct conversion type that directly converts the X-rays into electric signals; either type is applicable. The radiation detector 13 is provided to face the radiation source 11 with the subject M interposed therebetween.

Here, the signal value of each pixel in an image obtained by the radiation detector 13 (pixel signal value) is the value obtained by converting the intensity of the radial rays having reached the radiation detector 13 into electric signals, that is, the value correlated with the intensity of the radial rays having reached the radiation detector 13, and the pixel signal value becomes higher as the reached radial rays have the higher intensity. On the other hand, in the present embodiment, the photographing console 2 and the diagnosis console 3 handle each pixel signal value as the value representing the absorbed dose. In other words, the photographing console 2 converts each pixel signal value of a series of frame images received by the communication unit 25 into a value representing the absorbed dose, and transmits the value to the diagnosis console 3. That is, in the photographing console 2 and the diagnosis console 3, as the absorbed dose is higher, the pixel signal value of the dynamic images becomes higher and is drawn white (at low density) on the image.

A reading control device 14 is connected to the photographing console 2. On the basis of an image reading condition input from the photographing console 2, the reading control device 14 controls the switching unit of each pixel of the radiation detector 13 to switch the reading of the electric signals accumulated in each pixel. By reading the electric signals accumulated in the radiation detector 13, the reading control device 14 obtains the image data. The image data correspond to the frame image. The reading control device 14 outputs the obtained frame image to the photographing console 2. The image reading condition is, for example, the frame rate, the frame interval, the pixel size, the image size (matrix size), or the like. The frame rate is the number of frame images to obtain per second and coincides with the pulse rate. The frame interval is the time after the start of one operation of obtaining the frame image and before the start of the next operation of obtaining the frame image, and coincides with the pulse interval.

The irradiation control device 12 and the reading control device 14 are connected to each other, and exchange synchronous signals with each other so that the irradiation operation and the image reading operation are synchronized with each other.

[Structure of Photographing Console 2]

The photographing console 2 outputs the irradiation condition and the image reading condition to the photographing device 1 to control the radiographing of the photographing device 1 and the operation of reading the radiographic image, and moreover displays the dynamic images obtained by the photographing device 1 so that a photographer such as a radiographer can check the positioning or whether the image is useful in diagnosis.

The photographing console 2 includes, as illustrated in FIG. 1, a control unit 21, a storage unit 22, a manipulation unit 23, a display unit 24, and a communication unit 25, and these units are connected through a bus 26.

The control unit 21 includes a CPU (Central Processing Unit), a RAM (Random Access Memory), and the like. In response to the manipulation of the manipulation unit 23, the CPU of the control unit 21 reads out the system program or various processing programs stored in the storage unit 22, develops the programs in the RAM, executes the various processes including a photographing control process to be described below in accordance with the developed programs, and intensively controls the operation of the units in the photographing console 2, and the irradiation operation and the reading operation of the photographing device 1.

The storage unit 22 includes a nonvolatile semiconductor memory, a hard disk, or the like. The storage unit 22 stores the various programs to be executed in the control unit 21, the parameters necessary to execute the programs, or the data of the process results or the like. For example, the storage unit 22 stores the programs to execute the photographing control process illustrated in FIG. 2. The storage unit 22 stores the irradiation condition and the image reading condition in association with the check target part (here, the chest part) and the kind of diagnosis target (for example, the ventilation and the blood flow). Various programs are stored in the readable program code format, and the control unit 21 sequentially executes the operation in accordance with the program code.

The manipulation unit 23 includes a keyboard having a cursor key, numeric keys, various function keys, or the like, and a pointing device such as a mouse, and outputs an instruction signal input by the key operation made through the keyboard or the mouse operation to the control unit 21. The manipulation unit 23 may include a touch panel on the display screen of the display unit 24, and in this case, the instruction signal input through the touch panel is output to the control unit 21.

The display unit 24 includes a monitor such as an LCD (Liquid Crystal Display), a CRT (Cathode Ray Tube), or the like, and displays the input instruction from the manipulation unit 23, the data, or the like in accordance with the instruction of the display signals input from the control unit 21.

The communication unit 25 includes a LAN adapter, a modem, a TA (Terminal Adapter), or the like and controls the data exchange between the devices connected to the communication network NT.

[Structure of Diagnosis Console 3]

The diagnosis console 3 is a dynamic analysis apparatus for supporting the doctor's diagnosis by: obtaining the dynamic images from the photographing console 2, analyzing the obtained dynamic images, and displaying the analysis result images.

The diagnosis console 3 includes, as illustrated in FIG. 1, a control unit 31, a storage unit 32, a manipulation unit 33, a display unit 34, and a communication unit 35, and these units are connected with a bus 36.

The control unit 31 includes a CPU, a RAM, and the like. In response to the manipulation of the manipulation unit 33, the CPU of the control unit 31 reads out the system program or various processing programs stored in the storage unit 32, develops the programs in the RAM, executes the various processes including an image analysis process to be described below in accordance with the developed programs, and intensively controls the operation of the units in the diagnosis console 3. The control unit 31 functions as an obtainment unit, a determination unit, and a correction unit.

The storage unit 32 includes a nonvolatile semiconductor memory, a hard disk, or the like. The storage unit 32 stores various programs including the program to execute the image analysis process in the control unit 31, the parameters necessary to execute the programs, or the data of the process results or the like. These various programs are stored in the readable program code format, and the control unit 31 sequentially executes the operation in accordance with the program code.

The storage unit 32 stores an emphasis level table 321 (see FIG. 5) expressing the relation between the movement amount M of the region of interest and the degree of emphasis (emphasis level) of the pixel signal value.

The manipulation unit 33 includes a keyboard having a cursor key, numeric keys, various function keys, or the like, and a pointing device such as a mouse, and an instruction signal input by the key operation made through the keyboard or the mouse operation is output to the control unit 31. The manipulation unit 33 may include a touch panel on the display screen of the display unit 34, and in this case, the instruction signal input through the touch panel is output to the control unit 31.

The display unit 34 includes a monitor such as an LCD, a CRT, or the like, and performs various displays in accordance with the instruction of the display signals input from the control unit 31.

The communication unit 35 includes a LAN adapter, a modem, a TA, or the like and controls the data exchange between the devices connected to the communication network NT.

[Operation of Dynamic Analysis System 100]

Next, the operation of the dynamic analysis system 100 is described.

(Operation of Photographing Device 1 and Photographing Console 2)

First, the photographing operation by the photographing device 1 and the photographing console 2 is described.

Figure 2:
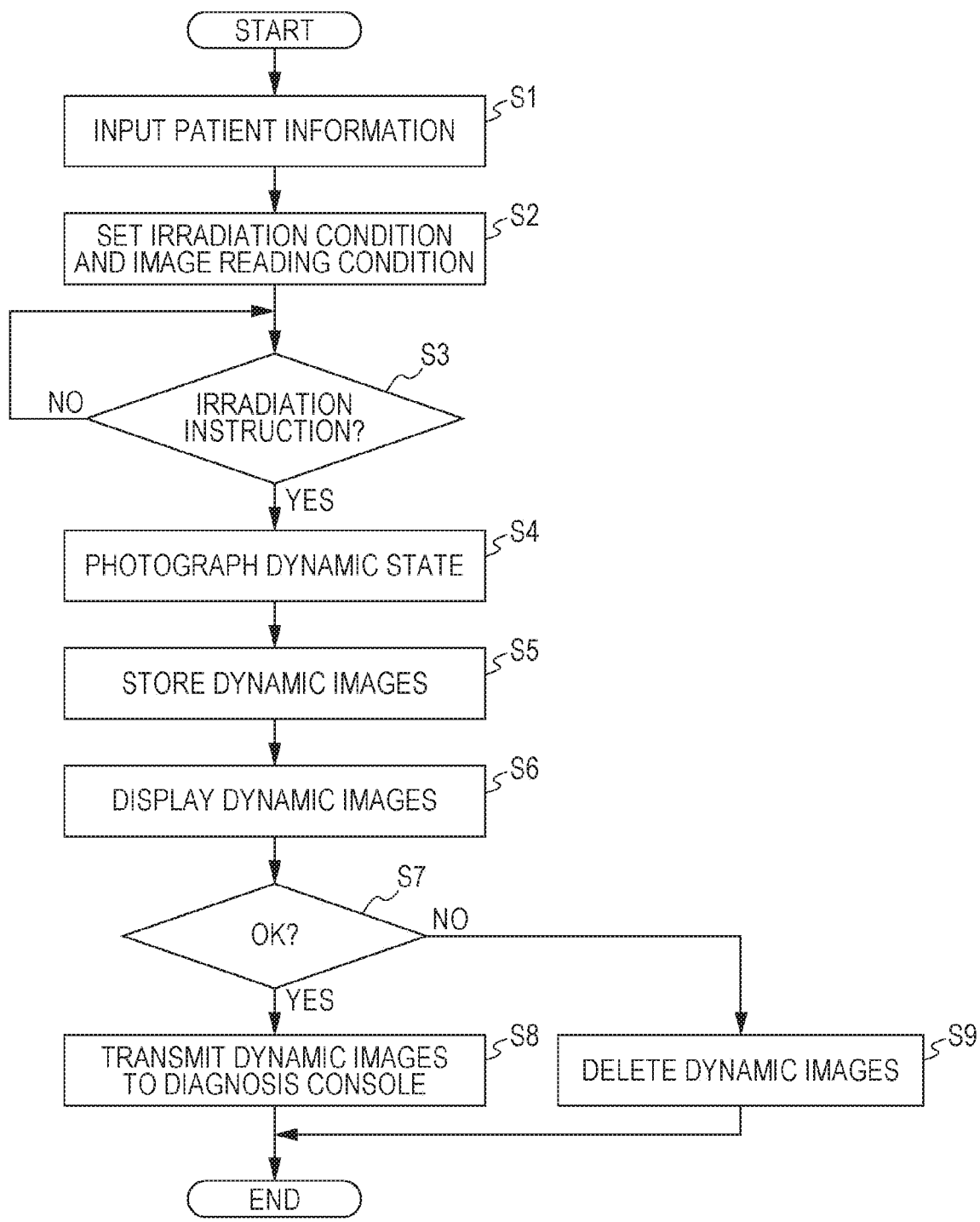
FIG. 2 is a flowchart showing a photographing control process to be executed by a control unit of a photographing console of FIG. 1.

FIG. 2 illustrates the photographing control process to be executed in the control unit 21 of the photographing console 2. The photographing control process is executed by the co-operation between the control unit 21 and the programs stored in the storage unit 22.

First, a photographer manipulates the manipulation unit 23 of the photographing console 2 to input pieces of patient information of a testee as the subject M (such as patient ID, name, body height, body weight, and sex), and the checkup information (the check target part (here, chest), and the kind of analysis target (ventilation, blood flow, or the like)) (step S1). The patient information and the checkup information may be received from the RIS (Radiology Information System) through the communication unit 25.

Next, based on the input checkup information, the irradiation condition is read out from the storage unit 22 and set to the irradiation control device 12 and the image reading condition is read out from the storage unit 22 and set to the reading control device 14 (step S2). Note that the irradiation condition and the image reading condition can be adjusted and set again by the photographer through the manipulation unit 23.

Next, the instruction of irradiation by the manipulation of the manipulation unit 23 is awaited (step S3). Here, the photographer places the subject M between the radiation source 11 and the radiation detector 13 and adjusts the positions. In the present embodiment, the photographing is performed while the testee (subject M) breathes, the photographer tells the subject to relax and breathe normally. If necessary, the photographer can tell the subject to breathe deeply by instructing "breathe in and breathe out". After the photographing preparation is completed, the photographer manipulates the manipulation unit 23 to input the radiation instruction.

Upon the input of the irradiation instruction by the manipulation unit 23 (YES in step S3), the photographing start instruction is output to the irradiation control device 12 and the reading control device 14 and thus the photographing of the dynamic state is started (step S4). That is to say, the radiation source 11 emits the radial rays at the pulse intervals set in the irradiation control device 12, and thus, the frame images are obtained by the radiation detector 13.

When the photographing of a predetermined number of frames is completed, the control unit 21 outputs the instruction of stopping the photographing to the irradiation control device 12 and the reading control device 14, and thus the photographing operation is stopped. The number of frames to be photographed is the number that can photograph at least one breathing cycle.

The frame images obtained by the photographing are sequentially input to the photographing console 2, and stored in the storage unit 22 in association with the number (frame number) expressing the photographing order (step S5), and are displayed in the display unit 24 (step S6). The photographer checks the positioning and the like by the displayed dynamic images, and determines whether the obtained image is suitable for the diagnosis (photographing: OK) or another photographing is necessary (photographing: FAIL). Then, the photographer manipulates the manipulation unit 23 to input the determination result.

When the determination result expressing the photographing: OK has been input by the predetermined manipulation of the manipulation unit 23 (YES in step S7), the pieces of information such as the identification ID for identifying the dynamic images, the patient information, the checkup information, the irradiation condition, the image reading condition, and the number expressing the photographing order (frame number) are added to each of a series of frame images obtained in the photographing of the dynamic state (for example, written in the header region of the image data), and the dynamic images are transmitted to the diagnosis console 3 through the communication unit 25 (step S8). Thus, the present process ends. On the other hand, when the determination result expressing the photographing: FAIL has been input by the predetermined manipulation of the manipulation unit 23 (NO in step S7), a series of frame images stored in the storage unit 22 is deleted (step S9) and the present process ends. In this case, another photographing is required.

(Operation of Diagnosis Console 3)

Next, description is made of the operation of the diagnosis console 3.

Upon the reception of a series of frame images of the dynamic images from the photographing console 2 through the communication unit 35, the diagnosis console 3 executes the image analysis process illustrated in FIG. 3 by the co-operation between the control unit 31 and the program stored in the storage unit 32.

Hereinafter, the image analysis process is described with reference to the flowchart of FIG. 3.

First, a pre-treatment is performed on the received dynamic images (step S10).

In the pre-treatment, the signal component (the ventilation signal component, the blood flow signal component) according to the kind of diagnosis target (ventilation, blood flow) is extracted.

First, each frame image of the dynamic images is divided into small regions with a predetermined size in accordance with the kind of diagnosis target, a representative value (for example, the average value, the central value, or the like) of the pixel signal values is calculated in the divided small region, and the pixel signal values in the small region are replaced by the calculated representative value. Thus, the signal component of the spatial frequency in accordance with the diagnosis target can be extracted. Next, the small regions of a series of frame images are related with each other, and in every small region, the time change of the pixel signal values in the region is filtered through a high-pass filter, a low-pass filter, or a band-pass filter in the time direction of the cut-off frequency in accordance with the kind of diagnosis target. Thus, the signal component of the time frequency in accordance with the kind of diagnosis target can be extracted.

Next, the dynamic images after the pre-treatment are analyzed and analysis result images are generated (step S11).

For example, analysis result images (interframe difference images) are generated in a manner that the difference of the pixel signal value is taken for each corresponding pixel between the adjacent frame images of the dynamic images (for example, from the pixel signal value of each pixel in the n-th frame image, the pixel signal value of the corresponding pixel in the (n−1)-th frame image (or before predetermined frames) is subtracted). Alternatively, the analysis result images may be generated by taking a difference of the pixel signal value for every corresponding pixel between each frame image of the dynamic images and the reference frame image. The analysis result images are not limited to a particular kind. Steps S10 and S11 may be omitted and the process may advance to step S12 directly.

Next, a pixel signal value correction process is executed (step S12).

FIG. 4 is a flowchart of a pixel signal value correction process A to be executed in step S12 in FIG. 3 in the first embodiment.

In the pixel signal value correction process A, first, the region of interest to which each pixel is related is set in the dynamic images after the pre-treatment, and the movement information of the set region of interest (movement amount M) is obtained (S1201).

In step S1201, for example, in the order from the upper left pixel of one frame image (for example, the first frame image), the pixel (attentional pixel) is related to the region of interest (for example, m×m pixels (m is a positive integer)) with that pixel serving as the center of the region of interest. Which part of other frame image corresponds to the set region of interest is specified by the template matching. Then, for example, the movement amount from the center of the region of interest in the (n−1)-th frame image to the center of the region of interest in the n-th frame image is obtained as the movement information of that region of interest in the n-th frame image (movement amount M). In this example, the movement amount M between the adjacent frame images is obtained but the movement amount M between the frame images that are separated from each other with a predetermined interval may be obtained alternatively.

Note that in the present embodiment, the region of interest to which each pixel of the dynamic images is related is set; however, it is only necessary that each pixel in at least the region of the check target part to be diagnosed is related to the region of interest. For example, since the check target part is the lung field in the present embodiment, the lung field region may be extracted and the region of interest may be set only in the lung field region.

Next, based on the obtained movement information of each region of interest, the emphasis level α of the pixel signal value of each pixel is determined (step S1202).

Figure 5:
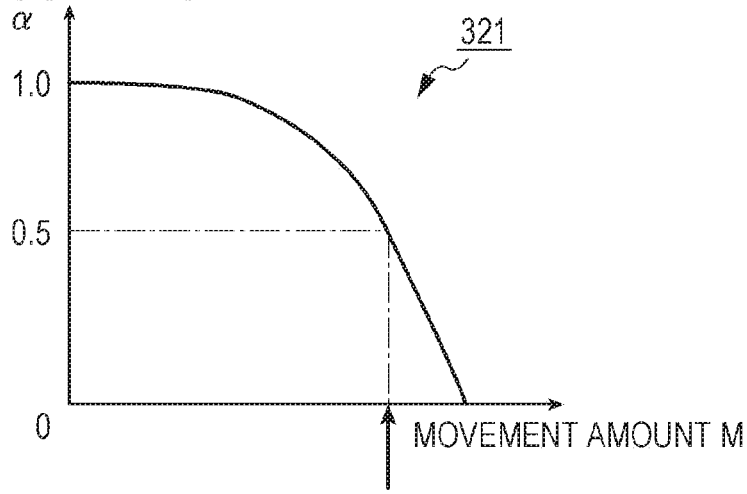
FIG. 5 is a diagram showing one example of an emphasis level table.

For example, with reference to the emphasis level table 321 stored in the storage unit 32, the emphasis level α in accordance with the movement amount M of the region of interest is determined as the emphasis level α of the pixel signal value of the attentional pixel related to that region of interest. FIG. 5 shows one example of the emphasis level table 321. For example, if the movement amount M is the value shown by the arrow in FIG. 5, the emphasis level α of the pixel signal value of the attentional pixel is 0.5. Although the emphasis level α for the movement amount M is shown as the graph in the emphasis level table 321 of FIG. 5, a list (table) in which the value of the movement amount M is related to the value of the emphasis level α may alternatively be formed.

Next, the pixel signal values of the analysis result images generated in step S11 are corrected based on the obtained emphasis level α of each pixel (step S1203), and thus the image analysis process ends.

In step S1203, the pixel signal value in(x1, y1) of the pixel (x1, y1) is corrected to the pixel signal value out(x1, y1) by the following (Formula 1):

$$\text{out}(x1, y1) = \alpha \times \text{in}(x1, y1) \qquad \text{(Formula 1)}$$

Here, the dynamic images of the chest part include, for example, the movements of the skeleton and the like along with the respiration and the pulsation of a heart. The artifact by these movements is emphasized by, for example, the analysis for the interframe difference or the like, and the emphasized artifact interrupts the observation of the signals which should be focused. As a result, the accuracy of analysis and diagnosis has deteriorated. In view of the above, as illustrated in FIG. 5, the pixel signal value is multiplied by the emphasis level α that is lower as the movement amount M is larger. This makes it possible to suppress the structure with the large movement such as the ribs that would interrupt the observation of the lesion from the analysis result images in a short time and with high accuracy without the bone suppression or the like, which would take time in the conventional technique.

The corrected analysis result images generated in the image analysis process are displayed on the display unit 34. The analysis result images displayed here are the images where the structure with the large movement such as the ribs that would interrupt the observation of the lesion has been suppressed. Thus, the doctor can observe the analysis result images easily and therefore the diagnosis performance can be improved.

Second Embodiment

Next, a second embodiment of the present invention will be described.

In the exhaling phase of the respiratory movement, the diaphragm and the lung tissue go up and the bones including the ribs, the collarbones, and the shoulders go down. In the inhaling phase, the diaphragm and the lung tissue go down and the bones including the ribs, the collarbones, and the shoulders go up. In the second embodiment, the emphasis level α of the pixel signal value is decreased in a region where the movement is in the direction opposite to the diaphragm, or the emphasis level α of the pixel signal value is decreased in a region where the movement is in the same direction as the shoulder, so that the structure that would interrupts the diagnosis of the ribs or the like is suppressed.

In the second embodiment, the storage unit 32 of the diagnosis console 3 stores an emphasis level table 322 (see FIG. 6) expressing the relation among the degree of direction difference φ and the movement amount M of the region of interest and the emphasis level α of the pixel signal value, or an emphasis level table 323 (see FIG. 7) expressing the relation among the degree of direction similarity θ and the movement amount M of the region of interest and the emphasis level α of the pixel signal value. The following description is made of the operation of the diagnosis console 3 according to the second embodiment. Other structure and photographing operation of the dynamic analysis system 100 are similar to those described in the first embodiment and the description in the first embodiment is cited.

In the second embodiment, the control unit 31 of the diagnosis console 3 executes an image analysis process shown in FIG. 3 described in the first embodiment; however, since the process to be executed in step S12 is different from that of the first embodiment, description is hereinafter made of a pixel signal value correction process B to be executed in step S12.

Figure 8:
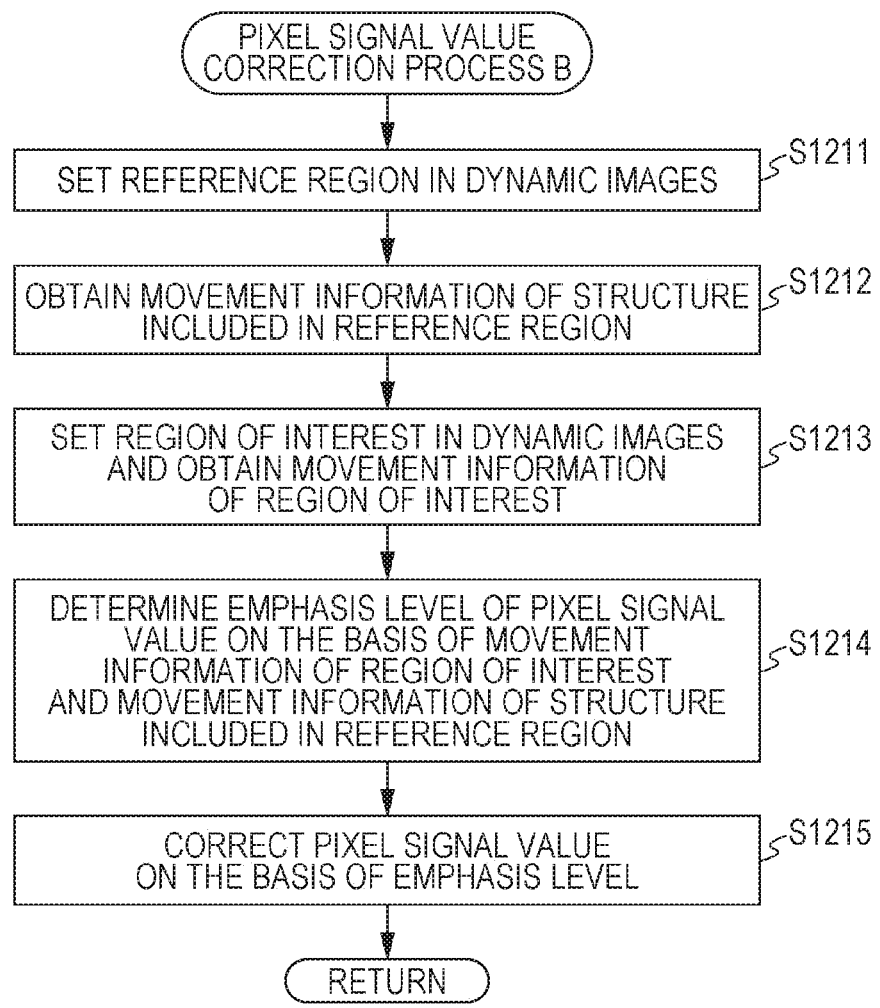
FIG. 8 is a flowchart showing a pixel signal value correction process B to be executed in step S12 in FIG. 3 according to a second embodiment.

FIG. 8 is a flowchart of the pixel signal value correction process B to be executed in step S12 in FIG. 3 in the second embodiment. The pixel signal value correction process B is executed by the co-operation between the control unit 31 and the programs stored in the storage unit 32. The control unit 31 functions as an obtainment unit, a determination unit, a correction unit, and a second obtainment unit by executing the pixel signal value correction process B.

First, a reference region is set in the dynamic images after the pre-treatment (step S1211).

The reference region is set in, for example, the diaphragm, the shoulder (body surface), or the like. For example, one frame image (for example, the first frame image) of the dynamic images is displayed on the display unit 34, and a line or a rectangle specified by the user manipulation in the manipulation unit 33 is set as the reference region. In regard to other frame images, the region at the same pixel position as the region specified in the first frame image is set as the reference region.

Figure 9:
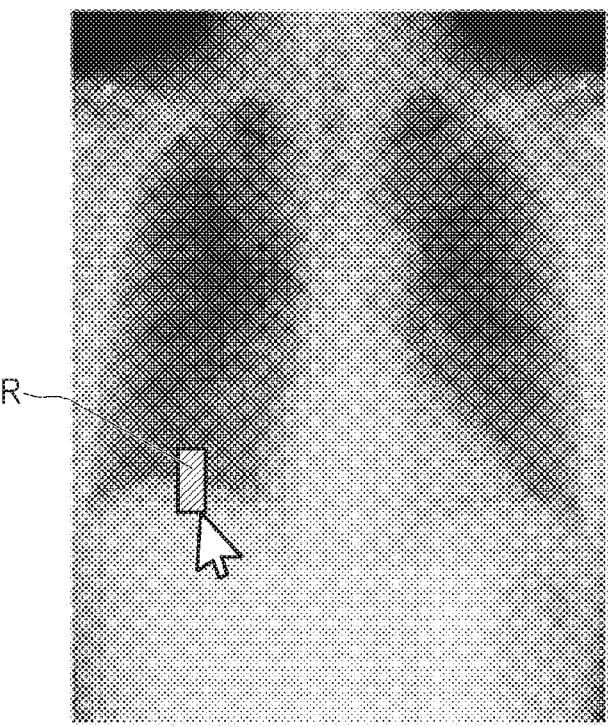
FIG. 9 is a diagram showing an example of setting a reference region in a diaphragm.
Figure 10:
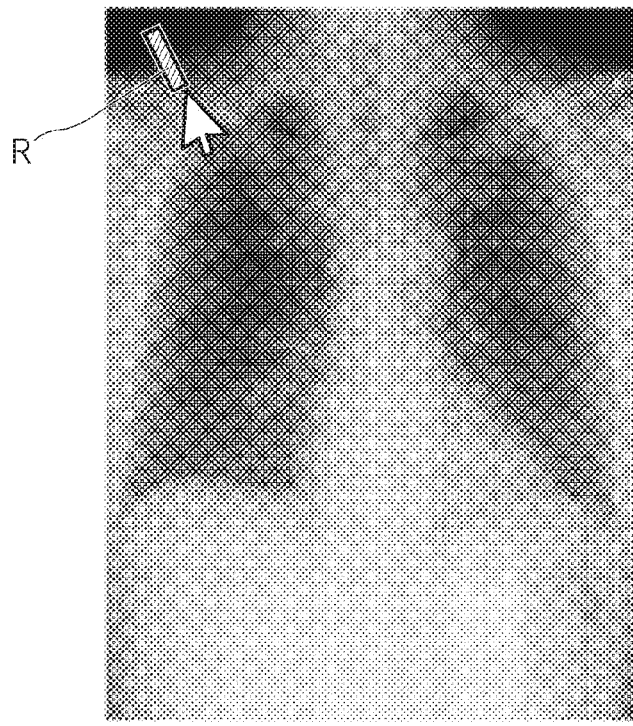
FIG. 10 is a diagram showing an example of setting a reference region in a shoulder.

If the reference region is set in the diaphragm region, the user specifies a line or a rectangle that is substantially parallel to the body axis near the diaphragm as the reference region as shown by R in FIG. 9. If the reference region is set in a shoulder region, the user specifies a line or a rectangle that is substantially perpendicular to the body surface line of the shoulder as shown by R in FIG. 10.

Note that the reference region may be automatically set by the control unit 31 instead of by the user manipulation.

Next, in the dynamic images after the pre-treatment, the movement information of the structure included in the reference region is obtained (step S1212).

Figure 11:
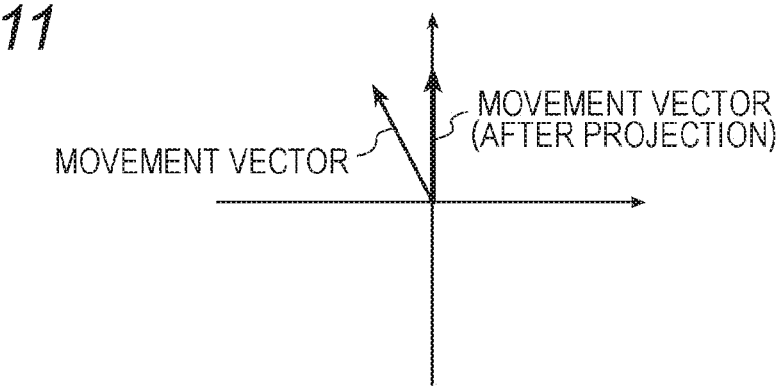
FIG. 11 is a diagram showing an example of projecting a movement direction to another axial direction.

For example, the most intensive edge is detected by the edge detection in each of the reference regions of the frame images of the dynamic images, and the movement direction of the most intensive edge between the frame images is obtained as the movement information of the structure included in the reference region. Here, the movement direction of the shoulder is in the oblique up-down direction but the data projected to another axis (for example, y axis) may be used as illustrated in FIG. 11. This can convert the movement in the oblique direction into the movement in the up-down direction, and the reference based on which the degree of direction similarity θ is calculated in the later process can be made in the up-down direction; thus, the pixel signal value of the bones such as the ribs moving in the up-down direction by the respiration can be easily suppressed.

Alternatively, the representative value (for example, the average value, the central value, or the like) of the pixel signal value in the reference region is calculated in each frame image of the dynamic images, and based on the difference value obtained by subtracting from the representative value calculated from the n-th frame image, the representative value calculated from the (n−1)th frame image, the movement direction of the structure included in the reference region can be specified, and the specified movement direction can be obtained as the movement information of the structure included in the reference region.

In the case where the diaphragm goes up, the lung field region also goes up following the diaphragm. Therefore, in the reference region set in the diaphragm, the proportion of the lung field region with the small pixel signal values decreases and the proportion of the white region below the diaphragm with the high pixel signal values increases; thus, the representative value of the pixel signal values increases. That is, if the reference region is set in the diaphragm and the difference value of the representative values of the reference region is positive, the movement direction of the diaphragm can be specified as the upward direction. On the other hand, in the case where the diaphragm goes down, the lung field region also goes down following the diaphragm. Therefore, in the reference region set in the diaphragm, the proportion of the lung field region with the small pixel signal values increases and the proportion of the white region below the diaphragm with the high pixel signal values decreases; thus, the representative value of the pixel signal values decreases. That is, if the reference region is set in the diaphragm and the difference value of the representative values of the reference region is negative, the movement direction of the diaphragm can be specified as the downward direction.

If the shoulder goes up, in the reference region set in the shoulder, the proportion of the through region (the region the radial rays have directly reached) decreases and the proportion of the human body region with the high pixel signal value (white region) increases; thus, the representative value of the pixel signal values increases. That is to say, if the reference region is set in the shoulder and the difference value of the representative value of the reference region is positive, the movement direction of the shoulder can be specified as the upward direction. If the shoulder goes down, in the reference region set in the shoulder, the proportion of the through region increases and the proportion of the human body region with the high pixel signal value decreases; thus, the representative value of the pixel signal values decreases. That is to say, if the reference region is set in the shoulder and the difference value of the representative values of the reference region is negative, the movement direction of the shoulder can be specified as the downward direction.

Next, in the dynamic images after the pre-treatment image, the region of interest to which each pixel is related is set and the movement information of the set region of interest (the movement amount M and the movement direction) is obtained (step S1213).

In step S1213, for example, in the order from the upper left pixel of the target region of the reference image (for example, the first frame image), the pixel (attentional pixel) is related to the region of interest (for example, m×m pixels (m is a positive integer)) with the pixel serving as the center of that region of interest. Which part of other frame image corresponds to the set region of interest is specified by the template matching. Then, for example, the movement amount M from the center position of the region of interest in the (n−1)-th frame image to the center position of the region of interest in the n-th frame image is obtained as the movement information of that region of interest in the n-th frame image. In this example, the movement amount M and the movement direction between the adjacent frame images are obtained but the movement amount between the frame images that are separated from each other with a predetermined interval may be obtained alternatively.

Next, based on the movement information of the obtained region of interest and the movement information of the structure included in the reference region, the emphasis level α of the pixel signal value of each pixel is determined (step S1214).

Figure 12:
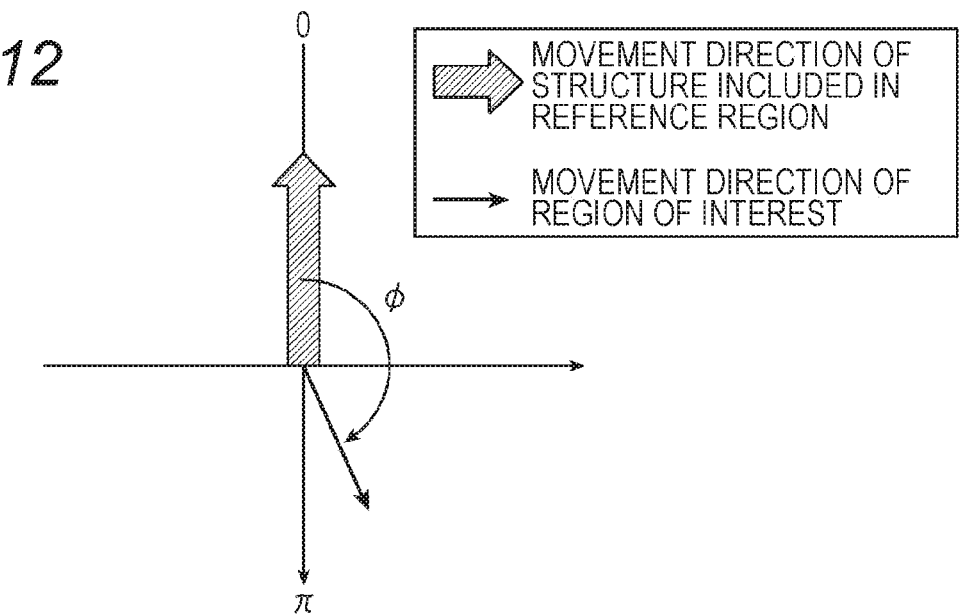
FIG. 12 is a diagram for describing the degree of direction difference.

For example, if the reference region is set in the diaphragm, first, the degree of direction difference φ(x1, y1) corresponding to the angle difference between the movement direction of the structure included in the reference region and the movement direction of the region of interest with the attentional pixel (x1, y1) serving as the center is calculated as shown in FIG. 12. Next, with reference to the emphasis level table 322 (see FIG. 6) stored in the storage unit 32, the emphasis level α(x1, y1) in accordance with the movement amount M(x1, y1) and the degree of direction difference φ(x1, y1) of the region of interest is determined as the emphasis level α of the pixel signal value of the attentional pixel related to that region of interest.

Figure 13:
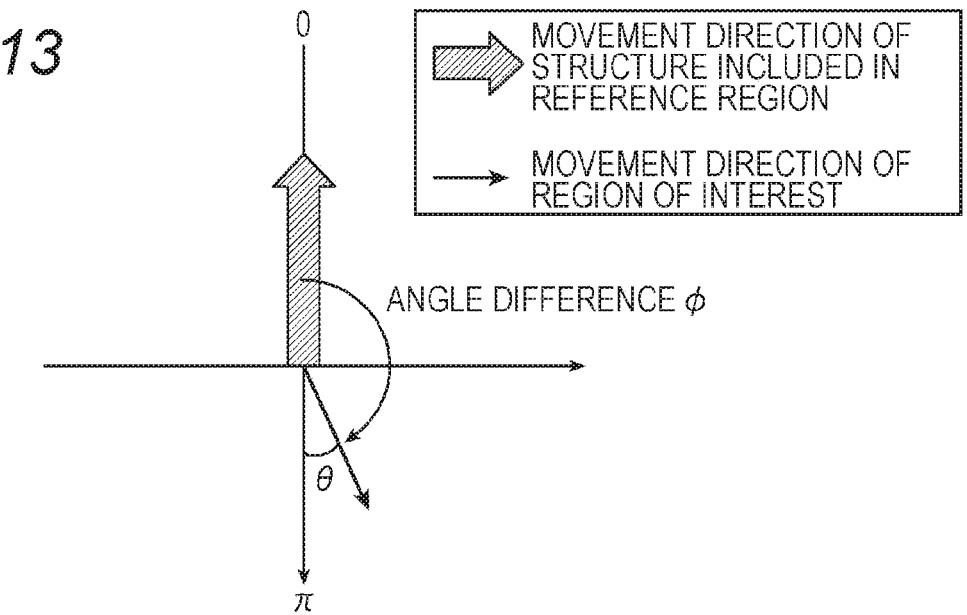
FIG. 13 is a diagram for describing the degree of direction similarity.

For example, if the reference region is set in the shoulder, first, the degree of direction similarity θ(x1, y1) is calculated by subtracting from π, the angle difference φ between the movement direction of the structure included in the reference region and the movement direction of the region of interest with the attentional pixel (x1, y1) serving as the center as illustrated in FIG. 13. Next, with reference to the emphasis level table 323 (see FIG. 7) stored in the storage unit 32, the emphasis level α(x1, y1) in accordance with the movement amount M(x1, y1) of the region of interest and the direction similarity θ(x1, y1) is determined as the emphasis level α of the attentional pixel related to that region of interest.

Note that even when the reference region is set in the shoulder, the degree of direction difference φ may be calculated and the emphasis level α may be determined using the emphasis level table 322 like in the case of the diaphragm. However, the graph shape of the emphasis level table 322 is different from that shown in FIG. 6.

Figure 6:
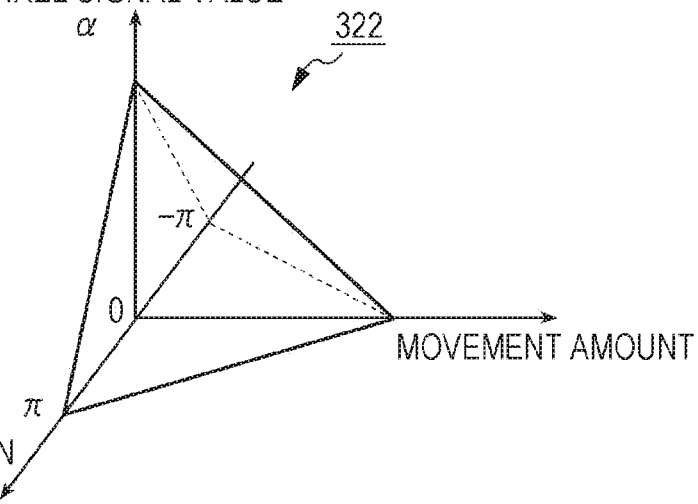
FIG. 6 is a diagram showing one example of an emphasis level table.
Figure 7:
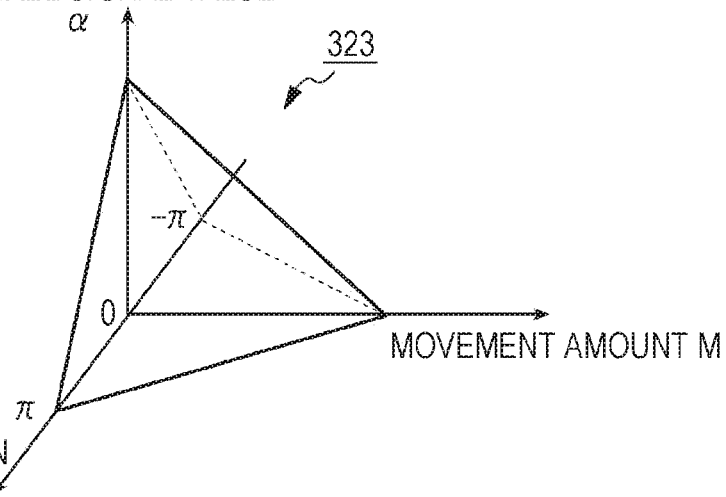
FIG. 7 is a diagram showing one example of an emphasis level table.

The emphasis level table 322 in FIG. 6 and the emphasis level table 323 in FIG. 7 show the emphasis level α relative to the movement amount M and the degree of direction difference φ (the degree of direction similarity θ) as a graph but may be a list (table) in which the value of the movement amount M and the degree of direction difference φ (the direction similarity θ) is related to the value of the emphasis level α.

Next, based on the emphasis level α of each pixel that is obtained, the pixel signal values of the analysis result images generated in step S11 are corrected (step S1215) and thus the image analysis process ends.

In step S1215, the pixel signal value in(x1, y1) of the attentional pixel (x1, y1) is corrected to the pixel signal value out(x1, y1) by the aforementioned (Formula 1).

Here, the dynamic images of the chest part include the movements of the skeleton and the like along with the respiration and the heart beating, for example, and the artifact by these movements is emphasized by the analysis of the interframe difference or the like, and the emphasized artifact interrupts the observation of the signal to be focused. Thus, the accuracy of analysis and diagnosis has deteriorated. In the respiration, the skeleton such as the ribs moves in a direction different from that of the diaphragm and moves in the same direction as that of the shoulder. In view of this, as shown in FIG. 6, the pixel signal value of the analysis result image is multiplied by the lower emphasis level α as the attentional pixel of the region of interest has the larger movement amount M and the larger degree of direction difference φ from the diaphragm (i.e., the angle difference from the diaphragm is larger). Alternatively, as shown in FIG. 7, the pixel signal value of the analysis result image is multiplied by the lower emphasis level α as the attentional pixel of the region of interest has the larger movement amount M and the larger degree of direction similarity θ to the shoulder (i.e., the angle difference from the shoulder is smaller). In this manner, the emphasis level α is determined by considering the movement direction of the region of interest in addition to the movement amount M of the region of interest; thus, the structure such as the ribs that would interrupt the observation of the lesion can be suppressed in a shorter time and with higher accuracy without the bone suppression or the like, which would take time in the conventional technique.

The corrected analysis result images generated in the image analysis process are displayed on the display unit 34. The analysis result images displayed here are the images where the structure such as the ribs that interrupts the observation of the lesion has been suppressed; thus, the doctor can observe the analysis result images easily and therefore the diagnosis performance can be improved.

Third Embodiment

Next, a third embodiment of the present invention will be described.

In the exhaling phase of the respiratory movement, the bones including the ribs, the collarbones, and the like go down. Moreover, since the air in the alveolus decreases, the density of the alveolus increases; thus, the pixel signal values between the ribs increase. On the other hand, in the inhaling phase of the respiratory movement, the bones including the ribs, the collarbones, and the like go up. Moreover, since the air in the alveolus increases, the density of the alveolus decreases; thus, the pixel signal values between the ribs decrease. In the third embodiment, the movement direction of the ribs is specified using this principle on the basis of the pixel signal values between the ribs, and by decreasing the emphasis level α of the pixel signal values in the region that moves in the same direction as the movement direction of the ribs, the structure that would interrupt the diagnosis, such as the ribs, is suppressed with high accuracy.

In the third embodiment, the storage unit 32 of the diagnosis console 3 stores the emphasis level table 323 expressing the relation between the degree of direction similarity θ and the movement amount M of the region of interest and the emphasis level α of the pixel signal value. The following description is made of the operation of the diagnosis console 3 according to the third embodiment. Other structure and photographing operation of the dynamic analysis system 100 are similar to those described in the first embodiment and the description in the first embodiment is cited.

In the third embodiment, the control unit 31 of the diagnosis console 3 executes the image analysis process shown in FIG. 3 described in the first embodiment but since the process executed in step S12 of FIG. 3 is different from that of the first embodiment, the following description is made of the pixel signal value correction process C to be executed in step S12.

Figure 14:
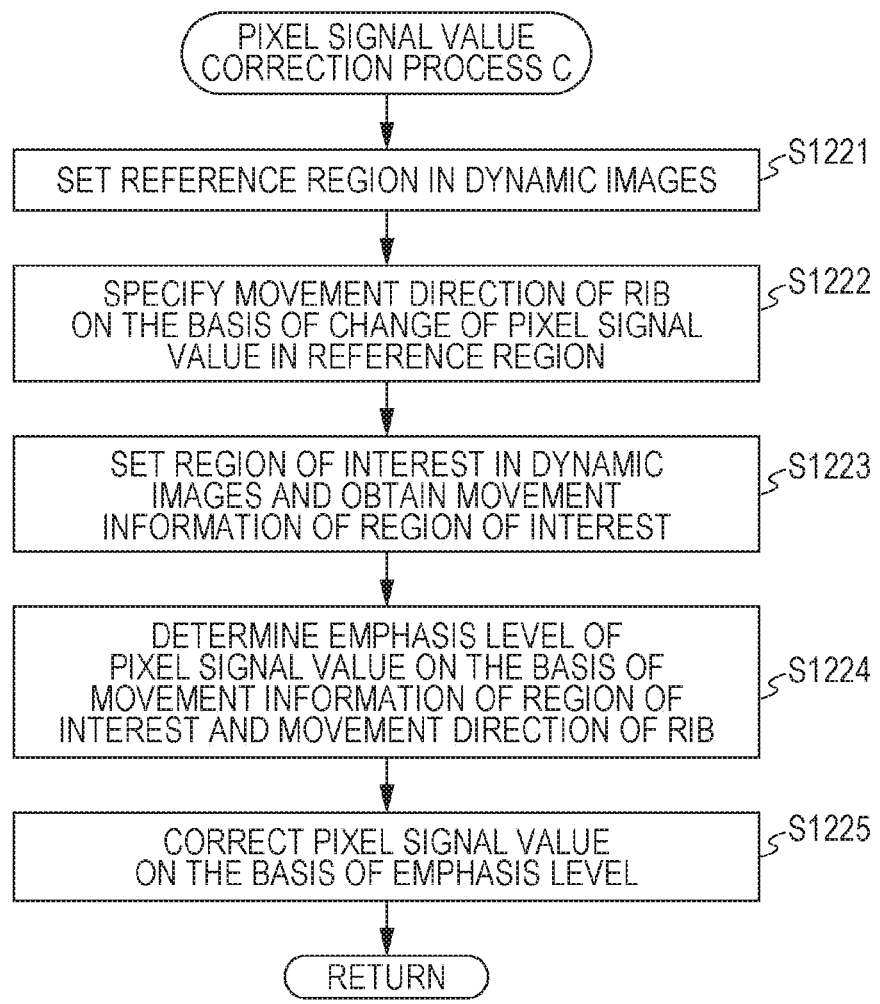
FIG. 14 is a flowchart showing a pixel signal value correction process C to be executed in step S12 in FIG. 3 according to a third embodiment.

FIG. 14 is a flowchart of the pixel signal value correction process C to be executed in step S12 in FIG. 3 in the third embodiment. The pixel signal value correction process C is executed by the co-operation between the control unit 31 and the programs stored in the storage unit 32. The control unit 31 functions as an obtainment unit, a determination unit, a correction unit, and a specification unit by executing the pixel signal value correction process C.

First, the reference region is set in the dynamic images after the pre-treatment (step S1221).

Figure 15:
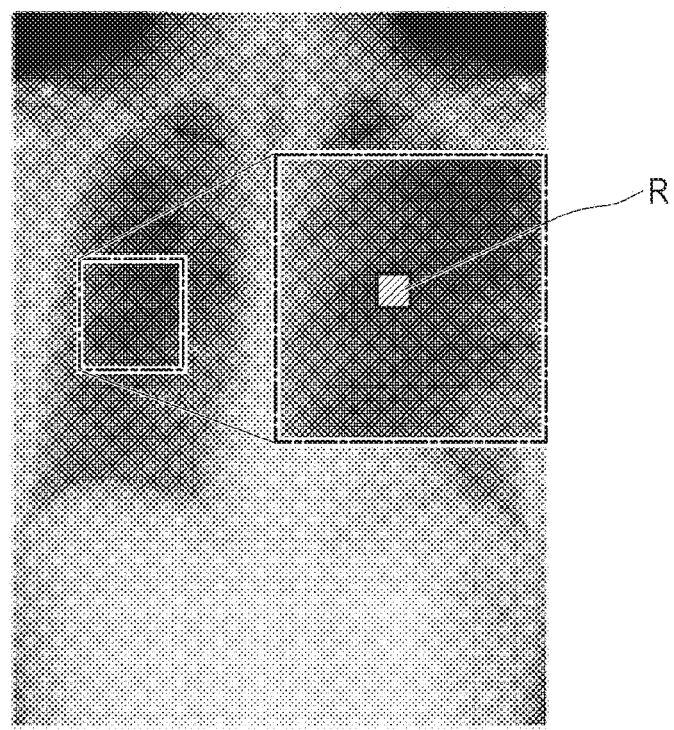
FIG. 15 is a diagram showing an example of setting a reference region in a region between ribs.

Here, the reference region is set between the ribs. For example, the display unit 34 displays one frame image of the dynamic images (for example, the first frame image) and the region between the ribs (for example, rectangular or circular region) specified by the user manipulation through the manipulation unit 33 is set as the reference region as shown by R in FIG. 15. Here, the user needs to specify the region which the ribs do not enter in all the frame images as the reference region. In regard to other frame images, the region at the same pixel position as the region specified in the first frame image is set as the reference region.

Note that the reference region may be automatically set by the control unit 31 instead of by the user manipulation.

Next, the movement direction of the ribs is specified based on the change of the pixel signal values in the reference region of the dynamic images after the pre-treatment (step S1222).

In step S1222, first, the representative value (for example, the average value, the central value, or the like) of the pixel signal values in the reference region is calculated in each frame image of the dynamic images after the pre-treatment, and the difference value is obtained by subtracting from the representative value calculated from the n-th frame image, the representative value calculated from the (n−1)th frame image. If the difference value is positive, the phase corresponds to the exhaling phase and in this case, the movement direction of the ribs is specified as the downward direction. If the difference value is negative, the phase corresponds to the inhaling phase and in this case, the movement direction of the ribs is specified as the upward direction.

Next, in the dynamic images after the pre-treatment, the region of interest to which each pixel is related is set and the movement information of the set region of interest (the movement amount M and the movement direction) is obtained (step S1223).

The process of step S1223 is similar to the process of step S1213; therefore, the description thereto is cited.

Next, based on the movement information of the region of interest and the movement information of the ribs that are obtained, the emphasis level α of the pixel signal value of each pixel is determined (step S1224).

First, the degree of direction similarity θ(x1, y1) is calculated by subtracting from 7C, the angle difference φ between the movement direction of the ribs and the movement direction of the region of interest with the attentional pixel (x1, y1) serving as the center. Next, with reference to the emphasis level table 323 stored in the storage unit 32, the emphasis level α(x1, y1) in accordance with the degree of direction similarity θ(x1, y1) and the movement amount M(x1, y1) of the region of interest is determined as the emphasis level α of the pixel signal value of that region of interest.

The emphasis level α may be determined using the emphasis level table 322 by setting the angle difference φ as the degree of direction difference φ. However, in this case, the graph shape of the emphasis level table 322 is different from that shown in FIG. 6.

Next, based on the obtained emphasis level α of each pixel, the pixel signal value of each pixel in the analysis result images generated in step S11 is corrected (step S1225), and thus the image analysis process ends.

In step S1225, the pixel signal value in(x1, y1) of the region of interest (x1, y1) is corrected to the pixel signal value out(x1, y1) by the aforementioned (Formula 1).

Here, in the third embodiment, the movement direction of the ribs is specified based on the change of the pixel signal values in the region between the ribs where the pixel signal values expressing the density change of the lung can be obtained without the influence from the ribs. Then, the pixel signal value of the analysis result image is multiplied by the lower emphasis level α as the attentional pixel of the region of interest has the larger movement amount M and the larger degree of direction similarity θ to the ribs (i.e., the angle difference from the ribs is smaller). In this manner, the emphasis level α is derived by considering the movement direction of the region of interest in addition to the movement amount M of the region of interest; thus, the structure such as the ribs that would interrupt the observation of the lesion can be suppressed in a shorter time and with higher accuracy without the bone suppression or the like, which would take time in the conventional technique.

The corrected analysis result images generated in the image analysis process are displayed on the display unit 34. The analysis result images displayed here are the image where the structure such as the ribs that interrupts the observation of the lesion has been suppressed; thus, the doctor can observe the analysis result images easily and therefore the diagnosis performance can be improved.

As described above, the control unit 31 of the diagnosis console 3 sets the region of interest in the dynamic images of the chest part, obtains the movement information on the movement of the region of interest, and determines the emphasis level of the pixel signal values of the attentional pixel related to the region of interest on the basis of the obtained movement information of the region of interest. Based on the determined emphasis level, the pixel signal values of the attentional pixel of the analysis result images such as the interframe difference images generated by analyzing the dynamic images are corrected.

Thus, the structure such as the ribs that would interrupt the observation of the lesion can be suppressed in a shorter time and with higher accuracy without the bone suppression or the like, which would take time in the conventional technique.

For example, the control unit 31 determines the emphasis level of the pixel signal value of the attentional pixel to be a lower emphasis level as the movement amount of the region of interest is larger. Therefore, the structure with the large movement such as the ribs that would interrupt the observation of the lesion can be suppressed.

Moreover, for example, the control unit 31 sets the reference region in the dynamic images, obtains the movement information on the movement of the structure included in the reference region, and determines the emphasis level of the pixel signal value of the attentional pixel related to the region of interest on the basis of the movement information of the region of interest and the movement information of the structure included in the reference region. Therefore, the structure such as the ribs that would interrupt the observation of the lesion can be suppressed with higher accuracy.

For example, the control unit 31 sets the reference region in the region including the diaphragm in the dynamic images, obtains the movement direction of the diaphragm, and determines the emphasis level of the pixel signal value of the attentional pixel to be a lower emphasis level as the angle difference between the movement direction of the region of interest and the movement direction of the diaphragm is larger. Therefore, the structure such as the ribs whose movement direction is different from that of the diaphragm by a large angle can be suppressed with higher accuracy.

In another example, the control unit 31 sets the reference region in the region including the shoulder in the dynamic images, obtains the movement direction of the shoulder, and determines the emphasis level of the pixel signal value of the attentional pixel to be a lower emphasis level as the angle difference between the movement direction of the region of interest and the movement direction of the shoulder is smaller. Therefore, the structure such as the ribs whose movement direction is different from that of the shoulder by a small angle can be suppressed with higher accuracy.

In still another example, the control unit 31 sets the reference region in the dynamic images, specifies the movement direction of a predetermined structure on the basis of the change of the pixel signal values in the reference region, and determines the emphasis level of the attentional pixel related to the region of interest on the basis of the angle difference between the movement direction of the region of interest and the movement direction of the predetermined structure. For example, the reference region is set in the region between the ribs in the dynamic images, the movement direction of the ribs is specified based on the change of the pixel signal values in the reference region, and the emphasis level of the pixel signal value of the attentional pixel is determined to be a lower emphasis level as the angle difference between the movement direction of the region of interest and the movement direction of the ribs is smaller. Therefore, the ribs and the structure whose movement direction is different from that of the ribs by a small angle can be suppressed with higher accuracy.

Note that the present embodiment is about one example of the preferable dynamic analysis system according to the present invention, and is not limited to the system described herein.

For example, the above embodiments have described the example in which the dynamic images are the dynamic images of the chest but the dynamic images are not limited thereto and may be dynamic images of another part.

Although the above embodiments have described the example in which the pixel signal value of each pixel of the analysis result images is corrected based on the movement information of the region of interest or the movement information of the region of interest and the reference region, the signal to be corrected is not limited thereto and the pixel signal value of each pixel of the dynamic images obtained by photographing the dynamic state by the irradiation of a check target part with the radial rays may be corrected. This can suppress the structure with the large movement such as the ribs that would interrupt the observation of the lesion in the dynamic images.

Alternatively, the analysis result images may be obtained by correcting and then analyzing the pixel signal value of each pixel of the dynamic images according to the present invention.

The dynamic images obtained by photographing the dynamic state by the irradiation of the check target part with the radial rays according to the scope of claims in the present application include not just the dynamic images obtained from the radiation detector 13 by the photographing of the dynamic state (so-called raw data) but also the dynamic images obtained by processing the raw data (such as the process of converting the pixel signal value into the absorbed dose, or the image process typified by the aforementioned pre-treatment).

Although the above embodiments have described the example of performing the pre-treatment, the pre-treatment may be omitted in the present invention because this treatment is intended to increase the accuracy in obtaining the analysis result of ventilation and blood flow.

The first embodiment, the second embodiment, and the third embodiment may be used in combination.

Although the computer readable medium for the program according to the present invention is the hard disk, the semiconductor nonvolatile memory, or the like in the above description, the present invention is not limited thereto. Another computer readable medium such as a portable recording medium such as a CD-ROM is also applicable. A carrier wave is also applicable as the medium that provides the data of the program according to the present invention through the communication line.

In regard to other detailed structure and operation of the devices included in the dynamic analysis system 100, various changes can be made without departing from the concept of the present invention.

Although the present invention has been described and illustrated in detail, it is clearly understood that the same is by way of illustrated and example only and is not to be taken byway of limitation, the scope of the present invention being interpreted by terms of the appended claims.

What is claimed is:

1. A dynamic analysis apparatus comprising:
a control unit and a storage unit, the control unit processing a program stored in the storage unit and being operable as:
an obtainment unit configured to set a region of interest in a dynamic image obtained by photographing a dynamic state by irradiation of a check target part with radial rays, and obtain movement information on movement of the region of interest between frame images of the dynamic image;
a determination unit configured to determine an emphasis level of a pixel signal value of an attentional pixel corresponding to a pixel in the region of interest on the basis of the movement information of the region of interest obtained by the obtainment unit, wherein the movement information includes a movement amount and the determination unit determines the emphasis level to be a lower emphasis level as the movement amount of the region of interest is larger; and
a correction unit configured to correct the pixel signal value of the attentional pixel of the dynamic image or analysis result images generated by analyzing the dynamic image, on the basis of the emphasis level determined by the determination unit.

2. The dynamic analysis apparatus according to claim 1, wherein the control unit is further operable as
a second obtainment unit configured to set a reference region in the dynamic images, and obtain movement information on movement of a structure included in the reference region, wherein
the determination unit determines the emphasis level on the basis of the movement information of the region of interest and the movement information of the structure included in the reference region.

3. The dynamic analysis apparatus according to claim 2, wherein
the movement information of the region of interest and the movement information of the structure included in the reference region include a movement direction, and
the determination unit determines the emphasis level on the basis of an angle difference between the movement direction of the region of interest and the movement direction of the structure included in the reference region.

4. The dynamic analysis apparatus according to claim 3, wherein
the dynamic images are dynamic images of a chest part,
the second obtainment unit sets a reference region in a region including a diaphragm of the dynamic images and obtains a movement direction of the diaphragm, and
the determination unit determines the emphasis level to be a lower emphasis level as the angle difference between the movement direction of the region of interest and the movement direction of the diaphragm is larger.

5. The dynamic analysis apparatus according to claim 3, wherein
the dynamic images are dynamic images of a chest part,
the second obtainment unit sets a reference region in a region including a shoulder of the dynamic images and obtains a movement direction of the shoulder, and
the determination unit determines the emphasis level to be a lower emphasis level as the angle difference between the movement direction of the region of interest and the movement direction of the shoulder is smaller.

6. The dynamic analysis apparatus according to claim 3, wherein
the determination unit determines the emphasis level in accordance with a relation table or graph expressing the emphasis level relative to the movement information of the region of interest and the angle difference.

7. The dynamic analysis apparatus according to claim 3, wherein
the determination unit determines the emphasis level in accordance with a relation table or graph expressing the emphasis level relative to the movement information of the region of interest and an angle obtained by subtracting the angle difference from $\pi$.

8. The dynamic analysis apparatus according to claim 1, wherein
the movement information includes a movement direction,
the control unit is further operable as a specification unit configured to set a reference region in the dynamic images and specify a movement direction of a predetermined structure on the basis of a change of a pixel signal value in the reference region, and
the determination unit determines the emphasis level on the basis of an angle difference between the movement direction of the region of interest and the movement direction of the predetermined structure.

9. The dynamic analysis apparatus according to claim 8, wherein
the dynamic images are dynamic images of a chest part,
the specification unit sets the reference region in a region between ribs of the dynamic images and specifies a movement direction of the ribs on the basis of the change of the pixel signal value in the reference region, and
the determination unit determines the emphasis level to be a lower emphasis level as the angle difference between the movement direction of the region of interest and the movement direction of the ribs is smaller.

10. The dynamic analysis apparatus according to claim 1, wherein
the determination unit determines the emphasis level in accordance with a relation table or graph expressing the emphasis level relative to the movement information of the region of interest.

11. The dynamic analysis apparatus according to claim 1, wherein
the analysis result image is an interframe difference image generated by calculating a difference value of corresponding pixels between frame images in the dynamic images.

12. The dynamic analysis apparatus according to claim 1, wherein the correction unit corrects the pixel signal value by multiplying the pixel signal value by the emphasis level.

* * * * *